(12) United States Patent
Alas

(10) Patent No.: US 8,424,544 B2
(45) Date of Patent: Apr. 23, 2013

(54) TOOTHPICK WITH FLOSS

(76) Inventor: Abdulrahman Alas, Bakersfield, CA (US)

( * ) Notice: Subject to any disclaimer, the term of this patent is extended or adjusted under 35 U.S.C. 154(b) by 0 days.

(21) Appl. No.: 13/068,219

(22) Filed: May 4, 2011

(65) Prior Publication Data
US 2012/0279518 A1   Nov. 8, 2012

(51) Int. Cl.
  *A61C 15/00* (2006.01)
(52) U.S. Cl.
  USPC ............................ 132/321; 132/323; 132/329
(58) Field of Classification Search .......... 132/321–329
  See application file for complete search history.

(56) References Cited

U.S. PATENT DOCUMENTS

| | | | | |
|---|---|---|---|---|
| 2,648,341 A * | 8/1953 | Moll | ............................. | 132/323 |
| 3,902,510 A * | 9/1975 | Roth | ............................. | 132/322 |
| 6,250,313 B1 * | 6/2001 | Rees | ............................. | 132/321 |
| 2004/0168703 A1 * | 9/2004 | Cho | ............................. | 132/323 |
| 2006/0070636 A1 * | 4/2006 | Peters, Jr. | ...................... | 132/324 |

\* cited by examiner

*Primary Examiner* — Robyn Doan
(74) *Attorney, Agent, or Firm* — Raymond Y. Chan; David and Raymond Patent Firm

(57) ABSTRACT

An oral hygiene device, which is embodied as a toothpick with floss, includes a toothpick body and a floss. The toothpick body has a closed end, an opening end, and a floss cavity formed between the closed end and the opening end, wherein the closed end of the toothpick body forms a tapering end. The floss, having a first end and an opposed second end, is received in the floss cavity of the toothpick body in a hidden manner. The toothpick body is used as a conventional toothpick to effectively remove detritus and plaques from the teeth and is easy to carry. The floss is normally protected within the toothpick body in a hidden manner to keep the floss in a hygiene purpose and is adapted for being pulled out of the floss cavity for flossing.

12 Claims, 8 Drawing Sheets

TOOTHPICK WITH FLOSS

BACKGROUND OF THE PRESENT INVENTION

1. Field of Invention

The present invention relates to an oral hygiene tool, and more particular to a toothpick with floss, which forms in a compact structure for easy carrying and packaging.

2. Description of Related Arts

Gum disease is one of the common dental problems. Periodontal disease, especially in the early stages, is usually not painful such that many people having gum disease do not even realize it. Researchers report that the gum disease is an infection in the gums caused by the bacteria in plaque, wherein plaque and bacteria build up on and between the teeth. To prevent the gum disease, dentists always suggest having a better oral hygiene by brushing and flossing regularly. Accordingly, detritus should be removed from the teeth after a meal in order to prevent the plaque from being built-up. By removing detritus from your teeth, you can reduce the amount of plaque in your mouth.

Accordingly, toothpicks are considered as the common tool to remove detritus from the teeth, wherein the toothpick generally has one or two sharp ends to insert between teeth to pick up the detritus. Toothpick is a small elongated stick able to effectively remove detritus and plaques from the teeth and is easy to carry. In addition, the toothpicks can be contained in bunch form for packaging. However, holding a toothpick with the user's hand does not allow the user reach all necessary places in the mouth. In other words, it is hard to maneuver the toothpick towards the back of the mouth, and to clean the inside of the teeth. In particular, because of the elongated structure of the toothpick, it is inability for the toothpick to clean properly the space behind the wisdom teeth.

Floss, such as a dental floss, is an alternative tool to remove hard-to-reach plaque and/or detritus that toothpick misses. Dental floss is a thin nylon filament adapted to insert between the teeth and scrap along the teeth sides where the toothpick cannot reach. However, flosses are hard to be used. The user must wrap the floss around the middle fingers and must use the thumb to guide the floss in the right places. Therefore, many user neglect the use of floss since flossing requires more time and efforts.

Researches also report that the most effective way to remove plaque is to use both toothpicks and flossing. An improved oral hygiene tool, such as floss pick, combines both the toothpick and floss in one device, wherein the floss pick generally comprises a body having a tapering end in the shape of the toothpick, and two prongs at the opposed end to hold the floss between the prongs. However, the size of floss pick is relatively large in comparison with the toothpick. Therefore, the user will carry the conventional toothpick instead of the floss pick. In addition, the length of the floss is fixed by the distance between the prongs to limit the scraping movement along the teeth sides. The flossing angle of the floss pick is also limited by the arch shaped of the body. Therefore, it is hard to maneuver the flossing angle to scrap along the teeth sides. Most importantly, the floss is normally exposed to the surroundings such that dirt and germs will being attached to the floss.

SUMMARY OF THE PRESENT INVENTION

The invention is advantageous in that it provides a toothpick with floss, which forms in a compact structure for easy carrying and packaging.

Another advantage of the invention is to provide a toothpick with floss, which combines both toothpick and floss features in one single device.

Another advantage of the invention is to provide a toothpick with floss, wherein the floss is normally protected within the toothpick body in a hidden manner to keep the floss in a hygiene purpose.

Another advantage of the invention is to provide a toothpick with floss, wherein the using length of floss is adjustable according to the user preference.

Another advantage of the invention is to provide a toothpick with floss, wherein the toothpick body also forms a floss retention frame to hold the floss at different flossing angles.

Another advantage of the invention is to provide a toothpick with floss, which further provides a blushing element along the floss for the user to blush the space between teeth during flossing.

Another advantage of the invention is to provide a toothpick with floss, which does not require to alter the original structural design of the toothpick, so that the present invention is able to incorporate with the conventional toothpick container and the conventional toothpick packaging method.

Another advantage of the invention is to provide a toothpick with floss, wherein no expensive or complicated structure is required to employ in the present invention in order to achieve the above mentioned objects. Therefore, the present invention successfully provides an economic and efficient solution for providing a compact configuration for combining the toothpick with floss.

Additional advantages and features of the invention will become apparent from the description which follows, and may be realized by means of the instrumentalities and combinations particular point out in the appended claims.

According to the present invention, the foregoing and other objects and advantages are attained by an oral hygiene device, which comprises a toothpick body and a floss.

The toothpick body has a closed end, an opening end, and a floss cavity formed between the closed end and the opening end, wherein the closed end of the toothpicks forms a tapering end The floss, having a first end and an opposed second end, is received in the floss cavity of the toothpick body in a hidden manner, wherein the floss is adapted for being pulled out of the floss cavity.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1:
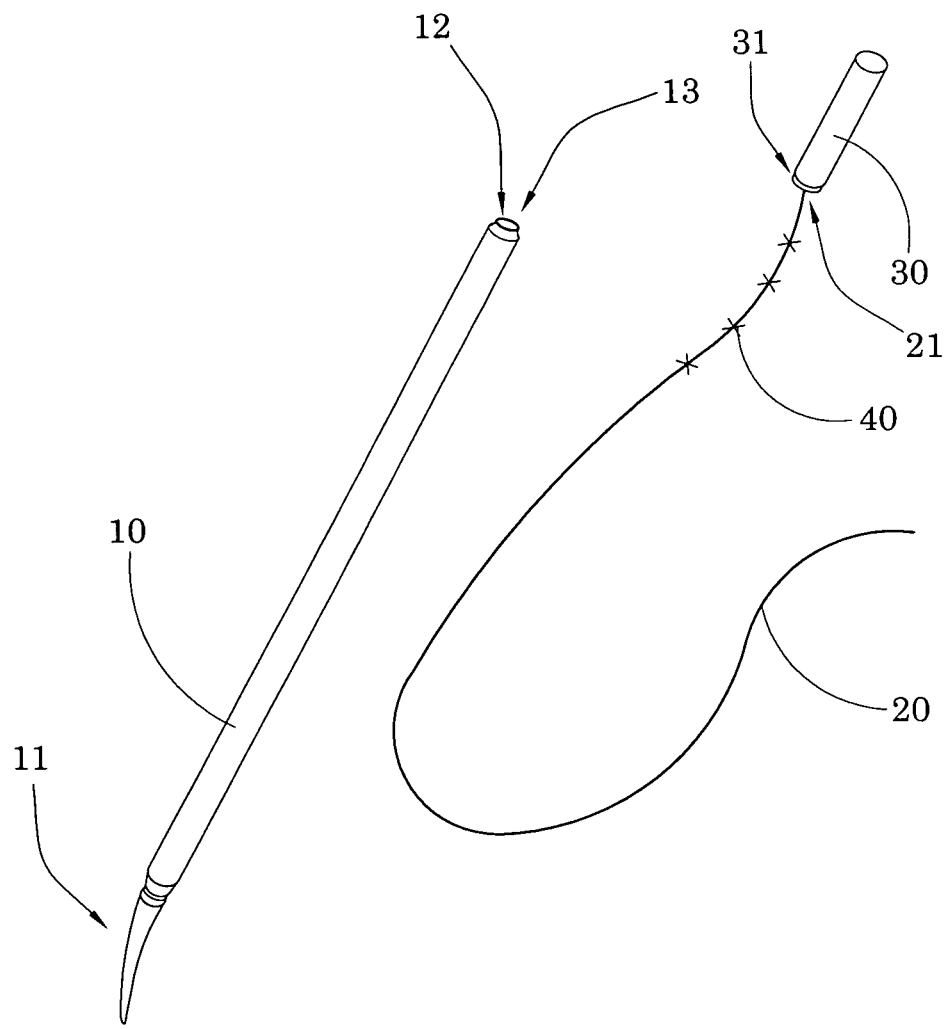
FIG. 1 is a perspective view of a toothpick with floss according to a first preferred embodiment of the present invention.
Figure 2:
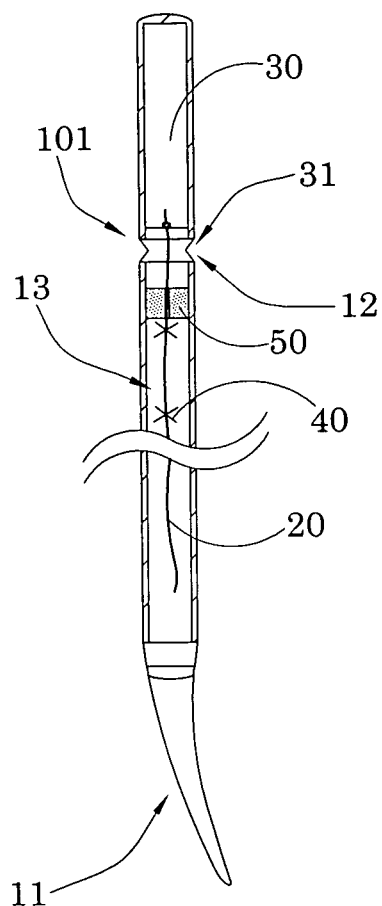
FIG. 2 is a sectional of a toothpick with floss according to the above first preferred embodiment of the present invention.

Referring to FIG. 1 of the drawings, an oral hygiene device, particularly to a toothpick with floss, according to a first preferred embodiment of the present invention is illustrated, wherein the oral hygiene device comprises a toothpick body 10 and a floss 20.

The toothpick body 10 has an elongated structure adapted for a user's hand to hold the toothpick body 10 as a conventional toothpick. The toothpick body 10 has a closed end 11, an opening end 12, and a floss cavity 13 formed between the closed end 11 and the opening end 12, wherein the closed end 11 of the toothpick body 10 forms a tapering end. The tapering end of the toothpick body 10 is a sharp end to insert between teeth to pick up the detritus. Accordingly, the toothpick body 10 forms with the structure of the conventional toothpick to effectively remove detritus and plaques from the teeth and is easy to carry. In addition, the toothpick bodies 10 can be contained in bunch form for packaging. In addition, the closed end 11 of the toothpick body 10 is an angled tapering end such that the user is able to maneuver the toothpick body 10 towards the back of the mouth and to clean the inside of the teeth, especially to clean properly the space behind the wisdom teeth.

The floss 20 is an elongated filament defining a first end 21 and an opposed second end 22 adapted to insert between the teeth and scrap along the teeth sides where the toothpick body 10 cannot reach easily. The floss 20 can be flavored or unflavored, and waxed or unwaxed. Also, the floss 20 can be configured as an elongated thread structure or an elongated flat structure.

According to the preferred embodiment, the floss 20 is received in the floss cavity 13 of the toothpick body 10 in a hidden manner, such that the floss 20 is normally stored and concealed within the floss cavity 13 to keep the floss 20 clean. In order to use the floss 20, the floss 20 is adapted for being pulled out of the floss cavity 12 through the opening end 12 of the toothpick body 10.

As shown in FIG. 1, the oral hygiene device further comprises a handle cap 30 detachably coupled at the opening end 12 of the toothpick body 10 to enclose the floss cavity 13, wherein the first end 21 of the floss 20 is fixed to a detachable end 31 of the handle cap 30 such that when the detachable end 31 of the handle cap 30 is detached from the toothpick body 10, the floss 20 is pulled out of the floss cavity 13.

Accordingly, the handle cap 30 is normally coupled with the toothpick body 10, wherein a breakable notch 101 is formed between the handle cap 30 and the toothpick body 10. When a bending force is applied at the breakable notch 101, the handle cap 30 is detached from the toothpick body 10. In other words, the breakable notch 101 is formed at the connection between the opening end 12 of the toothpick body 10 and the detachable end 31 of the handle cap 30.

According to the preferred embodiment, the second end 22 of the floss 20 is a free end that the second end 22 is not fixed to the toothpick body 10, such that the floss 20 can be entirely pulled out from the floss cavity 13 of the toothpick body 10 so as to use the floss 20 as the conventional dental floss. Preferably, the length of the floss 20 is longer than the length of the toothpick body 10.

The oral hygiene device further comprises a plurality of bristles 40 radially and outwardly extended from at least a portion of the floss 20 for performing brushing action during flossing. The bristles 40 are preferably formed at one end portion of the floss 20, preferably close to the first end 21 of the floss 20, such that when the floss 20 is inserted between the teeth, the bristles 40 are guided for fitting between the teeth and around the gum line to perform the brushing and/or flossing action at the same time so as to remove the detritus and/or plaque on the teeth. It is appreciated that the bristles 40 can be provided along the floss 20 between the first and second ends 21, 22 thereof.

According to the preferred embodiment, the oral hygiene device further comprises a solution absorber 50 presoaked with washing solution, wherein the solution absorber 50 is supported within the floss cavity 13 of the toothpick body 10 preferably close to the opening end 12 thereof to contact with the floss 20. When the floss 20 is pulled out from the floss cavity 13, the floss 20 is guided to contact with the solution absorber 50 for enabling the washing solution coating on the floss 20. The solution absorber 50 preferably is a sponge or the like, wherein the washing solution can be retained by the solution absorber 50 for a predetermined time period. Accordingly, the washing solution can be water or medicament commonly used for removing oral bacterial and bad breath. Therefore, when the floss 20 fits between the teeth and gum line during flossing, the washing solution coated at the floss 20 not only penetrates through the area between the teeth and around the gum line to remove the stain and bad breath, but also functions as a lubricant to minimize the friction between the floss 20 with the bristles 40 and the gum line so as to control gum disease and reduce uncomfortable feeling to the user. It is worth mentioning that when the floss 20 is pulled out from the floss cavity 13, the solution absorber 50 not only contacts with the floss 20 but also contacts with the bristles 40 such that the washing solution will be coated on the floss 20 and retained at the bristles 40 as well.

It is worth mentioning that the floss 20, the bristles 40 the solution absorber 50 are concealed within the floss cavity 13 of the toothpick body 10 before the handle cap 30 is broken or detached therefrom, so as to prevent any contaminant entering into the floss cavity 13.

Figure 3:
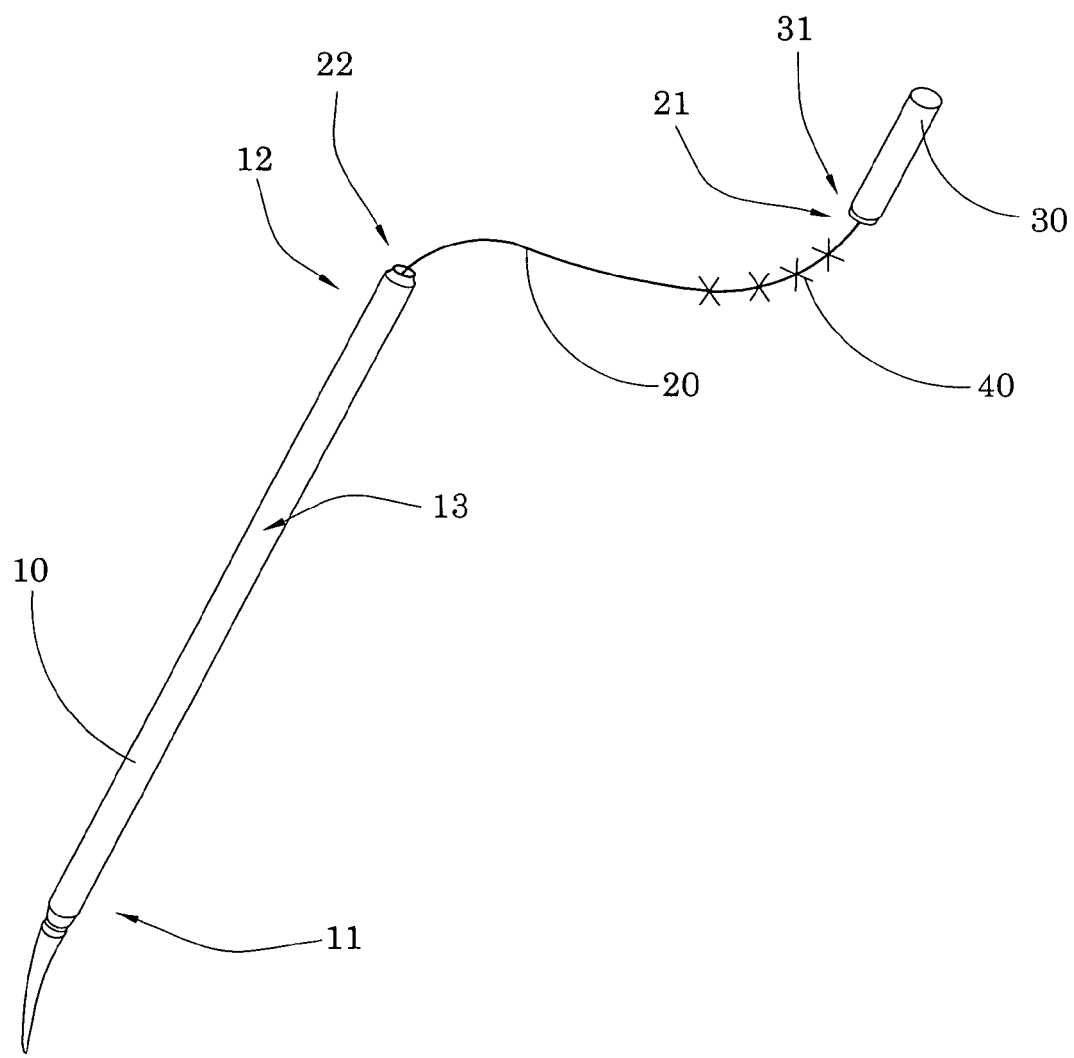
FIG. 3 is a perspective view of the toothpick with floss according to a second preferred embodiment of the present invention.

As shown in FIG. 3, an oral hygiene device according to a second embodiment illustrates an alternative mode of the first embodiment, wherein the second embodiment is a modification of the first embodiment. As shown in FIG. 3, the second end 22 of the floss 20 is fixed at the toothpick body 10 at a position close to the opening end 12 thereof for preventing the floss 20 being completely pulled out of the floss cavity 13. Therefore, the user is able to hold the toothpick body 10 and the handle cap 30 by two hands to maneuver the floss 20 for flossing.

Figure 4:
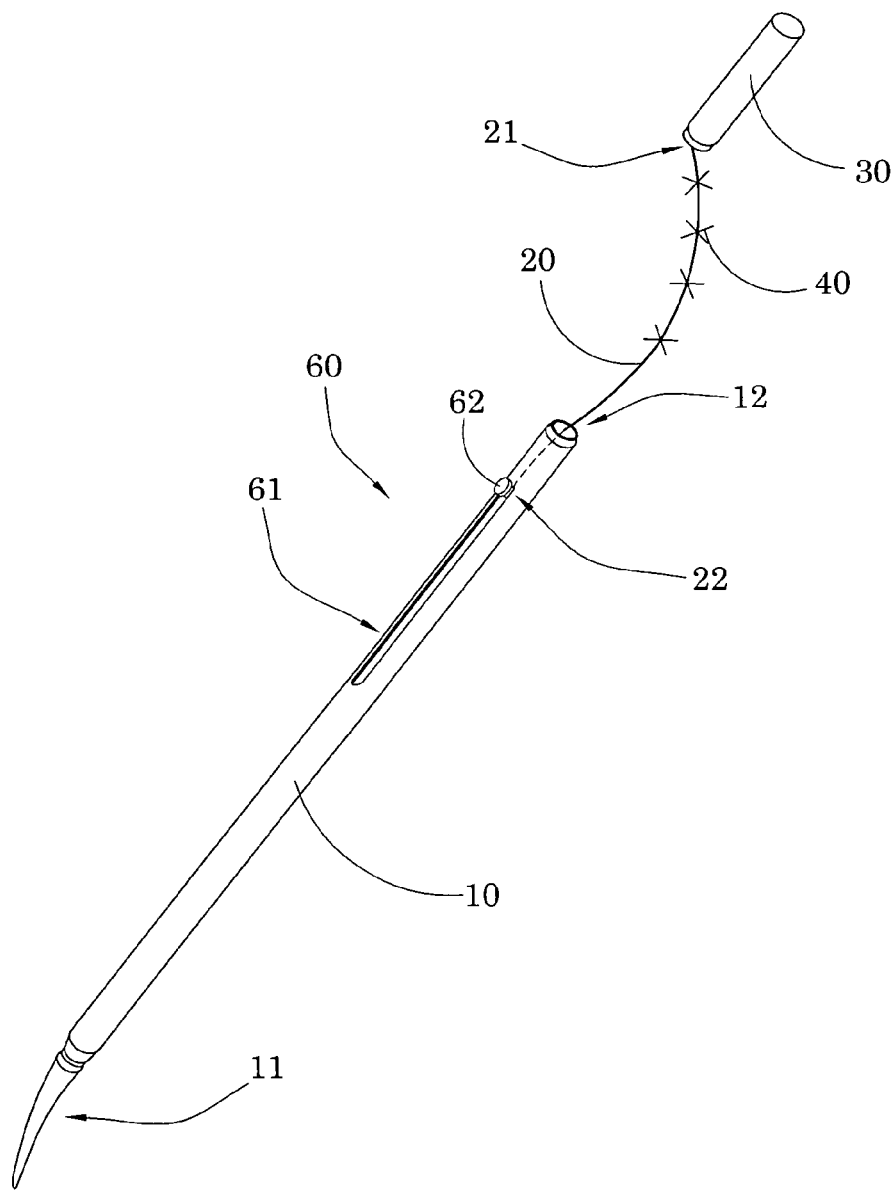
FIG. 4 is a perspective view of a toothpick with floss according to a third preferred embodiment of the present invention.
Figure 5:
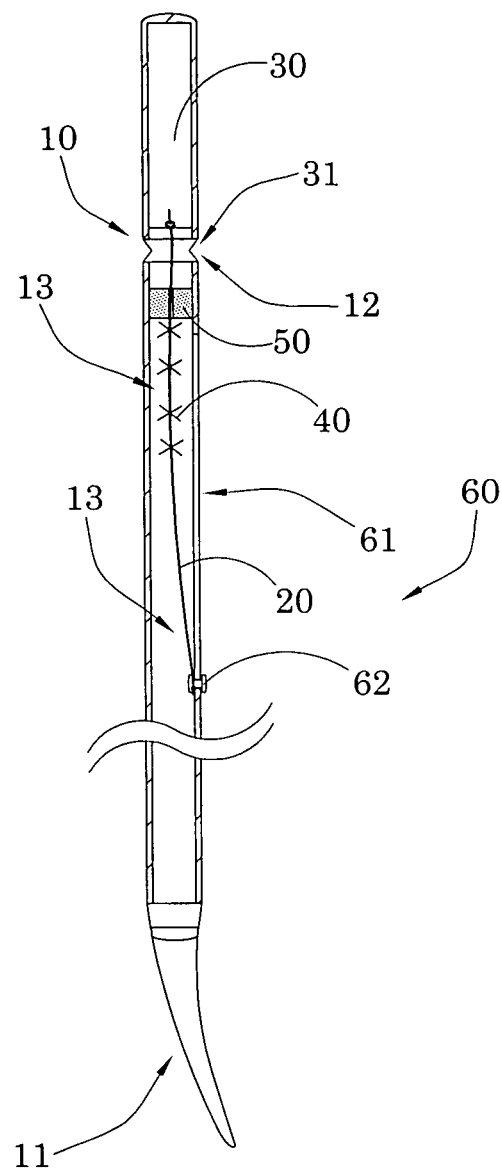
FIG. 5 is a sectional view of the toothpick with floss according to the above third preferred embodiment of the present invention.

As shown in FIGS. 4 and 5, an oral hygiene device according to a third embodiment illustrates an alternative mode of the second embodiment, wherein the third embodiment is a further modification of the first embodiment.

As shown in FIG. 4, the oral hygiene device further comprises a guiding arrangement 60 for retracting the floss 20 back to the floss cavity 13 of the toothpick body 10. The guiding arrangement 60 has an elongated guiding slot 61 formed along the toothpick body 10 and comprises a slider member 62 which is slidably coupled along the guiding slot 61 and is coupled with the second end 22 of the floss 20.

The guiding slot 61 is an elongated straight through slot formed at the circumferential side of the toothpick body 10 between the closed end 11 and the opening end 12, wherein the guiding slot 61 has a predetermined length shorter than the length of the toothpick body 10. Accordingly, the guiding slot 61 can be an elongated spiral through slot formed at the circumferential side of the toothpick body 10. It is worth mentioning that the guiding slot 61 is extended along the toothpick body 10 toward the opening end 12 thereof such that the second end 22 of the floss 20 is fixed at the toothpick body 10 at a position close to the opening end 12 thereof when the slider member 62 is slid toward the opening end 12 of the toothpick body 10.

As shown in FIG. 5, the slider member 62 has an inner coupling portion positioned within the floss cavity 13 to couple with the second end 22 of the floss 20 and an outer actuation portion extended out of the floss cavity 13 through the guiding slot 61. Accordingly, when the floss 20 is pulled out from the opening end 12 of the toothpick body 10, the slider member 62 is slid along the guiding slot 61 toward the opening end 12 of the toothpick body 10. When the slider member 62 is slid toward the tapering end (the closed end 11) of the toothpick body 10, the floss 20 is retracted back to the floss cavity 13. It is worth mentioning that by sliding the slider member 62 along the guiding slot 61, the user is able to slidably control a length of the floss 20 being pulled out at the opening end 12 of the toothpick body 10. In addition, the length of the guiding slot 61 should be corresponding to the length of the floss 20 being pulled out from the opening end 12 of the toothpick body 10.

Figure 6:
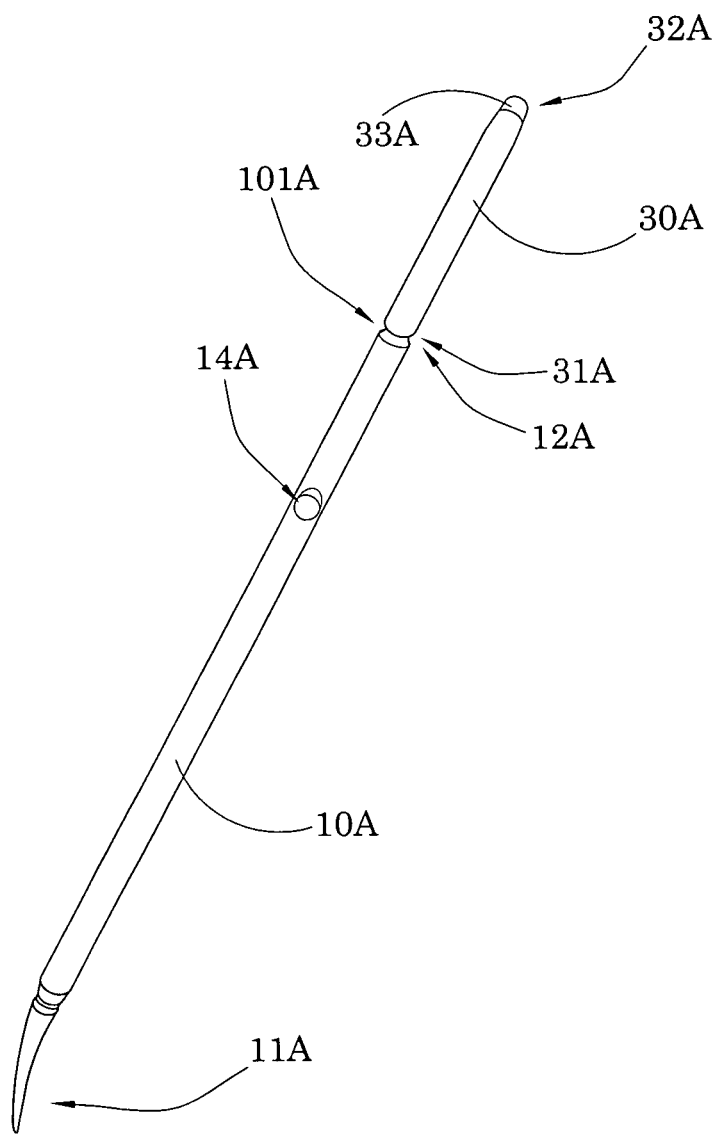
FIG. 6 is a perspective view of a toothpick with floss according to a fourth preferred embodiment of the present invention.
Figure 7:
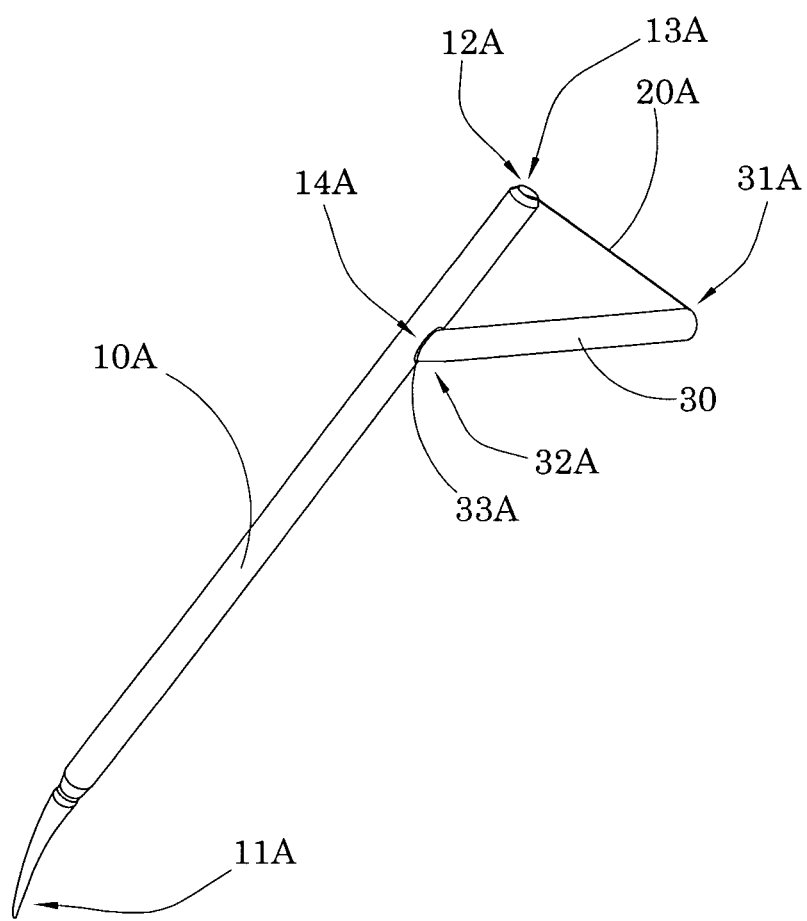
FIG. 7 is a perspective view of the toothpick with floss according to the above fourth preferred embodiment of the present invention, illustrating the y-shaped configuration of the toothpick body and the handle cap.

As shown in FIGS. 6 and 7, an oral hygiene device according to a fourth embodiment illustrates an alternative mode of the second embodiment, wherein the toothpick body 10A has a closed end 11A, an opening end 12A, and a floss cavity 13A. The floss 20A has a first end 21A fixed to the detachable end 31A of the handle cap 30A and a second end 22A fixed at the toothpick body 10A at a position close to the opening end 12A thereof. The floss 20A is received in the floss cavity 13A of the toothpick body 10A in a hidden manner and is normally stored and concealed within the floss cavity 13A to keep the floss 20A clean, wherein the floss 20A is adapted for being pulled out of the floss cavity 13 A through the opening end 12A of the toothpick body 10A.

The breakable notch 101A is formed at the connection between the opening end 12A of the toothpick body 10A and the detachable end 31A of the handle cap 30A, such that when the bending force is applied at the breakable notch 101A, the handle cap 30A is detached from the toothpick body 10A.

The toothpick body 10A further has a retention hole 14A formed between the opening end 12A and the closed end 11A, wherein when the handle cap 30A is detached from the toothpick body 10A, a free end 32A of the handle cap 30A is slidably inserted into the retention hole 14A to form a y-shaped configuration with the toothpick body 10A that the floss 20A runs between the detachable end 32A of the handle cap 30A and the opening end 12A of the toothpick body 10A. Preferably, the retention hole 14A is inclinedly formed at the toothpick body 10A to align with the inserting direction of the free end 32A of the handle cap 30A.

In particular, when the free end 32A of the handle cap 30A is slidably inserted into the retention hole 14A, the handle cap 30A is inclinedly extended from the toothpick body 10A at the retention hole 14A thereof. Therefore, a part of the toothpick body 10A, the floss 20A and the handle cap 30A form a triangular configuration, such that the user is able to hold the toothpick body 10A at the closed end 11A thereof to maneuver the floss 20A for flossing.

In order to secure the insertion of the free end 32A of the handle cap 30A at the retention hole 14A, the handle cap 30A further comprises a stopper 33A provided at the free end 32A thereof to retain the handle cap 30A in position after the free end 32A of the handle cap 30A is inserted into the retention hole 14A of the toothpick body 10A. Accordingly, the stopper 33A can be an elastic element, such as rubber, to secure the connection of the free end 32A of the handle cap 30A at the retention hole 14A. It is appreciated that two or more retention holes 14A are spacedly formed at the toothpick body 10A such that the user is able to selectively insert the free end 32A of the handle cap 30A into one of the retention holes 14A to selectively adjust the inclination angle between the toothpick body 10A and the floss 20A so as to selectively control the flossing angle of the floss 20A during flossing.

It is worth mentioning that the bristles 40 are also provided at the floss 20A while the solution absorber 50 is also supported within the floss cavity 13A of the toothpick body 10A at a position close to the opening end 12A thereof to contact with the floss 20A.

Figure 8:
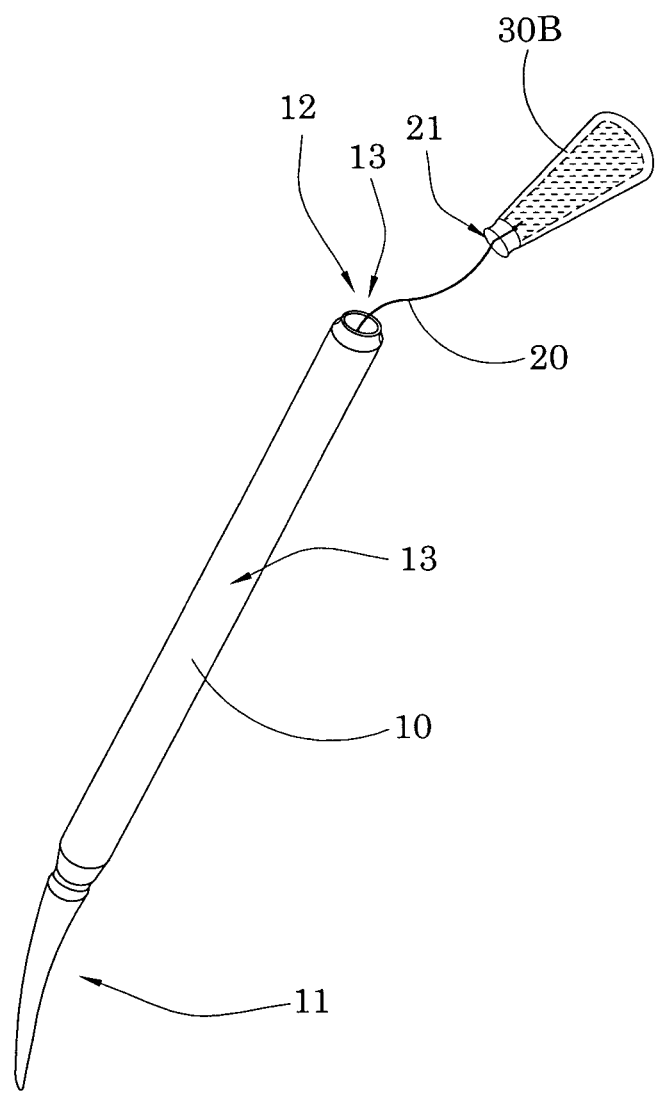
FIG. 8 is a perspective view of the toothpick with floss according to a fifth preferred embodiment of the present invention.

As shown in FIG. 8, an oral hygiene device according to a fifth embodiment illustrates an alternative mode of the second embodiment to show the alternative of the handle cap 30B. The handle cap 30B comprises a squeezable container for containing a predetermined amount of washing solution and is arranged in such a manner that when the handle cap 30B is squeezed, the washing solution is released to coat along the floss 20. Accordingly, the handle cap 30B is made of squeezable material, wherein the first end 21 of the floss 20 is fixed to the handle cap 30B while the second end 22 of the floss 20 is fixed at the toothpick body 10, such that when a squeezing force is applied at the handle cap 30B, the washing solution is released to flow along the floss 20. It is worth mentioning that the handle cap 30B has a squeezable opening where the second end 22 of the floss is fixed thereto such that when the squeezing force is applied at the handle cap 30B, the washing solution will discharge at the squeezable opening to flow along the floss 20. In addition, the user is able to detach the handle cap 30B from the toothpick body 10 before applying the squeezing force at the handle cap 30B. It is appreciated that the squeezing force can be applied at the handle cap 30B before the handle cap 30B is detached from the toothpick body 10, such that the washing solution is discharged to the floss cavity 13 so as to coat along the floss 20. It is worth mentioning that the solution absorber 50 is optional. When the solution absorber 50 is supported within the floss cavity 13 of the toothpick body 10, the solution absorber 50 will absorb the washing solution at the time the handle cap 30B is squeezed. In other words, the washing solution is not pre-soaked by the solution absorber 50.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An oral hygiene device, comprising:

a toothpick body having a closed end, an opening end, and a floss cavity formed between said closed end and said opening end, wherein said closed end of said toothpick body has a tapering end;

a floss, having a first end and an opposed second end, received in said floss cavity of said toothpick body in a hidden manner, wherein said floss is adapted for being pulled out of said floss cavity; and a handle cap detachably coupled at said opening end of said toothpick body to enclose said floss cavity, wherein said first end of said floss is fixed to a detachable end of said handle cap such that when said detachable end of said handle cap is detached from said toothpick body, said floss is pulled out of said floss cavity, wherein said toothpick body further has a retention hole formed between said opening end and said closed end, wherein when said handle cap is detached from said toothpick body, a free end of said handle cap is slidably inserted into said retention hole to form a y-shaped configuration with said toothpick body that said floss runs between said detachable end of said handle cap and said opening end of said toothpick body.

2. The oral hygiene device, as recited in claim 1, wherein said second end of said floss is fixed at said toothpick body at a position close to said opening end thereof for preventing said floss being completely pulled out of said floss cavity.

3. The oral hygiene device, as recited in claim 2, wherein said handle cap 25 further comprises a stopper provided at said free end thereof to retain said handle cap in position after said free end of said handle cap is inserted into said retention hole of said toothpick body.

4. The oral hygiene device, as recited in claim 3, wherein said tapering end of said toothpick body is an angled tapering end.

5. The oral hygiene device, as recited in claim 4, further comprising a plurality of bristles radially and outwardly extended from at least a portion of said floss for performing brushing action during flossing.

6. The oral hygiene device, as recited in claim 4, further comprising a solution absorber presoaked with washing solution, wherein said solution absorber is supported within said floss cavity and is arranged in such a manner that when said floss is pulled out from said floss cavity, said floss is guided to contact with said solution absorber for enabling said washing solution coating on said floss.

7. The oral hygiene device, as recited in claim 3, further comprising a plurality of bristles radially and outwardly extended from at least a portion of said floss for performing brushing action during flossing.

8. The oral hygiene device, as recited in claim 3, further comprising a solution absorber presoaked with washing solution, wherein said solution absorber is supported within said floss cavity and is arranged in such a manner that when said floss is pulled out from said floss cavity, said floss is guided to contact with said solution absorber for enabling said washing solution coating on said floss.

9. The oral hygiene device, as recited in claim 2, wherein said tapering end of said toothpick body is an angled tapering end.

10. The oral hygiene device, as recited in claim 2, further comprising a solution absorber presoaked with washing solution, wherein said solution absorber is supported within said floss cavity and is arranged in such a manner that when said floss is pulled out from said floss cavity, said floss is guided to contact with said solution absorber for enabling said washing solution coating on said floss.

11. The oral hygiene device, as recited in claim 1, wherein said handle cap further comprises a stopper provided at said free end thereof to retain said handle cap in position after said free end of said handle cap is inserted into said retention hole of said toothpick body.

12. The oral hygiene device, as recited in claim 11, wherein said tapering end of said toothpick body is an angled tapering end.

* * * * *